United States Patent [19]

Rittersdorf et al.

[11] 4,220,713

[45] Sep. 2, 1980

[54] STABILIZED DIAGNOSTIC AGENT

[75] Inventors: Walter Rittersdorf, Mannheim-Waldhof; Hugo Tiedemann, Mannheim-Wallstadt; Wolfgang Werner, Mannheim-Vogelstang; Hans Wielinger, Mannheim-Waldhof, all of Fed. Rep. of Germany

[73] Assignee: Boehringer Mannheim GmbH, Mannheim, Fed. Rep. of Germany

[21] Appl. No.: 892,362

[22] Filed: Mar. 31, 1978

[30] Foreign Application Priority Data

Apr. 9, 1977 [DE] Fed. Rep. of Germany ....... 2716060

[51] Int. Cl.² .......................... C12Q 1/54; C12Q 1/28
[52] U.S. Cl. ..................................... 435/14; 23/230 B; 252/408; 435/27; 435/805
[58] Field of Search ........... 195/99, 103.5 C, 103.5 R; 23/230 B; 252/408 R; 422/56, 57; 426/544; 435/10, 11, 14, 28

[56] References Cited

U.S. PATENT DOCUMENTS

| | | | |
|---|---|---|---|
| 3,489,684 | 6/1970 | O'Shea | 426/544 |
| 3,947,377 | 3/1976 | Werner et al. | 252/408 |
| 4,017,420 | 4/1977 | Bowie et al. | 252/408 |
| 4,089,747 | 5/1978 | Brushi | 195/99 |

OTHER PUBLICATIONS

Sokolova, et al., "Stability of Selenourea In Aqueous Solutions", *Chem. Abstracts,* vol. 83, No. 12, p. 435, (1975).

*Primary Examiner*—Thomas G. Wiseman
*Attorney, Agent, or Firm*—Sprung, Felfe, Horn, Lynch & Kramer

[57] ABSTRACT

The invention provides a diagnostic agent for the detection of (a) hydroperoxides or of substances which react with the liberation of hydroperoxides or of (b) peroxidase or of peroxidatively-active substances, comprising a stabilized oxidation indicator and, in case (a), peroxidase or a peroxidatively active substance or, in case (b), hydroperoxide or a substance which reacts with the liberation of hydroperoxides; wherein the stabilizer is a 1-arylsemicarbazide of the formula

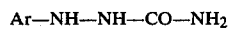

Ar—NH—NH—CO—NH₂ in which Ar is aryl or aryl substituted with alkyl, alkoxy or halogen.

7 Claims, No Drawings

STABILIZED DIAGNOSTIC AGENT

The present invention is concerned with an improved diagnostic agent. More specifically, the invention relates to agents for the detection of hydroperoxides or of substances which react with the liberation of hydroperoxides, as well as of peroxidase or of peroxidatively active substances, in body fluids, which agent contains an oxidation indicator as a chromogen.

The diagnostic agent according to the present invention is especially suitable for the detection of glucose in urine and blood, as well as for the detection of blood in urine, feces and liquors.

Rapid diagnostic agents have recently achieved very considerable importance in medical practice and in clinical laboratories and especially rapid tests based upon absorbent carriers. The absorbent carriers, which are usually paper, are impregnated with the reagents necessary for the detection reaction and show, after simple immersion into body fluids, a color reaction when the substance to be detected is present. Rapid tests which have achieved great importance in medical diagnosis are, in particular, rapid tests for the detection of glucose in urine and blood, as well as for the detection of blood in urine, feces and liquors.

These tests are based upon the following principle: in the case of the rapid tests for the detection of glucose in body fluids, for example, the glucose is oxidized by glucose oxidase (GOD) to give gluconic acid, atmospheric oxygen thereby being reduced to hydrogen peroxide. The hydrogen peroxide then oxidizes an oxidation indicator by means of peroxidase or of a peroxidate-active substance to give a color material, the depth of color of which is a measure of the amount of glucose present.

In the case of the detection of blood, the peroxidate properties of hemoglobin are utilized in order to oxidize the oxidation indicator with the help of a hydroperoxide.

Oxidation indicators for the above-mentioned rapid tests are generally known and fall within certain classes of compounds. Particularly usual are representatives of the benzidine series and heterocyclic azines, as well as phenolic bodies and especially the components of guaiac resin.

Due to their very nature, oxidation indicators are easily oxidizable substances. Therefore, it is not surprising that they can be oxidized by air, especially in the light. For these reasons, potentially useful oxidation indicators cannot necessarily be used for rapid diagnostic agents because their storage stability is very limited.

Therefore, the problem exists of finding appropriate protection for these oxidation indicators in order that they can be used for rapid diagnostic reagents without the sensitivity of the test being disadvantageously influenced by the amount of stabilizer added. The substances which ensure such a protection must, in turn, be sufficiently stable and must not uncontrollably or drastically change the sensitivity of the test papers.

Surprisingly, we have now found a group of 1-arylsemicarbazide compounds which bring about the desired effect in an outstanding manner.

Thus, according to the present invention, there is provided a diagnostic agent for the detection of hydroperoxides or of substances which react with the liberation of hydroperoxides or of peroxidase or of peroxidate-active substances in body fluids, using a stabilized oxidation indicator and using the reaction of a hydroperoxide or of a peroxidate-active substance with an oxidation indicator and evaluating the coloration produced by the reaction, wherein the stabilizer used is a compound of the general formula:

$$Ar-NH-NH-CO-NH_2 \qquad (I),$$

wherein Ar is an aryl radical optionally substituted by alkyl, alkoxy or halogen.

If desired, the diagnostic agent according to the present invention can also contain at least one member selected from buffers, wetting agents, thickening agents, protective colloids and complex formers.

By an aryl radical, there is preferably to be understood a phenyl or naphthyl radical; the alkyl and alkoxy radicals preferably contain up to 4 carbon atoms, the methyl and ethyl radicals being especially preferred. Halogen can be fluorine, chlorine or bromine, chlorine being preferred.

It is surprising that the 1-arylsemicarbazides (I) possess such outstandingly favorable properties. It was admittedly known that these compounds, as derivatives of hydrazine, have reducing properties; however, it has been shown that reducing agents are not automatically suitable for the purpose of stabilizing oxidation indicators without substantially influencing the sensitivity thereof. Thus, for example, the parent material of the series, i.e. semicarbazide, is not suitable for this purpose.

For quite a long time, other reducing agents, for example ascorbic acid, hydroquinone and other compounds, have been described as "modifiers" of the sensitivity of reactions (cf. German Patent Specification Nos. 1,129,003 and 2,555,704 and U.S. Pat. No. 3,008,879), but none of these compounds has been used in practice because, on the one hand, they are too unstable and, on the other hand, as a result of this instability during the time up to use, the sensitivity of the test is disadvantageously changed. Known anti-oxidants, for example nordihydroquaiaretic acid, N-phenyl-naphthylamine and mercapto compounds, as well as the compounds mentioned in U.S. Pat. No. 3,008,879 and in German Patent Specification No. 2,555,704, are not very suitable since they are either ineffective for the indicators used in rapid diagnostic agents or they are too unstable or they have too strong an influence on the reactivity.

The advantageous use of the stabilizers according to the present invention in test strips which contain oxidation indicators as chromogens is further explained in the following:

For the detection of blood or glucose, o-tolidine has hitherto been used in rapid tests as indicator. However, this carcinogenic substance has recently been replaced by 3,3',5,5'-tetramethylbenzidine (TMB) (cf. German Patent Specification No. 2,460,903).

Unfortunately, test papers with this indicator are, as in the case of all benzidine bodies, light-sensitive. Even after leaving in the light for a few minutes, they become discolored. An additional disadvantage is to be specially observed in the case of test papers for the detection of glucose, namely the ease with which the indicator is oxidized in the air and especially in the presence of atmospheric moisture. This phenomenon is very disadvantageous because it is precisely indicators for the detection of glucose in urine which come into the hands of lay persons for precautionary investigations.

Test papers which contain the 1-arylsemicarbazides (I) to be used according to the present invention surprisingly do not exhibit these disadvantages. Furthermore, the amount of 1-arylsemicarbazides (I) used in the test agents can be employed within wide limits of tolerance without substantially and disadvantageously influencing the sensitivity of the test agent.

In addition, the 1-arylsemicarbazides used according to the present invention are generally useful for glucose tests and for tests for the detection of blood in feces which contain, an indicators, heterocyclic azines, such as are described in German Patent Specifications Nos. 1,648,840 and 1,917,996. 1-[3-Alkylbenzthiazone-(2)]-2-[1-phenyl-3-methyl-4-ethyl-1,2,4-triazolone-(5)]-azines and 2,2'-azino-di-[1-ethyl-quinoline-(2)-disulphonic acid-(6)], have proved to be especially advantageous. They here also provide a greater stability towards discolorations brought about by light and air which, in turn, can easily give falsely positive reactions.

However, test papers for the detection of blood in feces preferably contain guaiac resin or a purified fraction thereof, namely guaiaconic acid A, with the specific extinction of $E_1$ $_{cm.}^{1\%}$ at 600 nm of at least 200, determined by the reaction with peroxidase and hydrogen peroxide. Such test papers also have a tendency to become blue colored in air and light, which can result in disturbances due to falsely positive reactions. Here, too, the 1-arylsemicarbazides (I) used according to the present invention prevent this disturbing and undesired blue coloration.

The test papers according to the present invention can be produced by known methods in which, to a particular formulation, there is added a 1-arylsemicarbazide (I) to be used according to the present invention (cf. German Patent Specifications Nos. 1,648,840; 1,917,996 and 2,460,903).

In general, the hydroperoxides used can be any of the conventional representatives of this class of compounds, when, like, for example, tert.-butyl hydroperoxide, they are not too volatile. In particular, there have proved to be useful the solid compounds 2,5-dimethylhexane-2,5-dihydroperoxide, tetraline hydroperoxide and diisopropylbenzene dihydroperoxide, as well as liquid representatives, for example diisopropyl-benzene hydroperoxide, cumol hydroperoxide, p-methane hydroperoxide and pinane hydroperoxide.

The hydroperoxides can be used in amounts of from 0.5 to 5 g. and preferably of 1 to 3 g. per 100 ml. of impregnation solution.

As buffers, there can be used, for example, citrate, phosphate, phthalate or succinate buffers.

It is also advantageous to add to the formulation small amounts (about 0.05 to 0.5 g. per 100 ml.) of a complex former, such as sodium metaphosphate or an alkali metal salt of ethylenediamine-tetraacetic acid, in order to avoid falsely positive reactions due to the presence of traces of metals. The complex formers can also act as buffers.

Since, due to the presence of relatively large amounts of water-soluble substances, the test papers can have a tendency to bleed, it is advisable to add thickening agents to the formulation, such as methyl cellulose or especially gelatine, in amounts of about 0.5 to 5 g. per 100 ml. In some cases, polyvinylpyrrolidone has also proved to be useful.

As wetting agent, it is preferable to use a longchained organic sulphate or sulphonate, for example sodium dodecyl-benzene-sulphonate, dioctyl-sodium sulphosuccinate or sodium lauryl sulphate.

For the production of the test papers according to the present invention, absorbent test papers, such as filter paper, cellulose or synthetic resin fleeces, are impregnated with solutions of the reagents in readily volatile solvents. This impregnation is preferably carried out in two stages, the compositions of the individual solutions depending upon the particular rapid test to be produced. For the production of a rapid test for the detection of blood in feces with the use of guaiac resin or guaiaconic acid A, it is advantageous when the hydroperoxide, in this case hydrogen peroxide, is not impregnated into the carrier but rather is added dropwise after application of the feces.

The 1-arylsemicarbazides used according to the present invention can be added in amounts of from about 5 to 900 mg. per 100 ml. of impregnation solution. Generally, the amount used depends upon the purpose for which the addition is made.

The 1-arylsemicarbazides used according to the present invention are either known or can be prepared analogously to known processes (see O. Widman, Ber., 26, 2613/1893; J. T. Hewitt, J. Chem. Soc., 209/1891).

The following Examples are given for the purpose of illustrating the present invention, the percentages therein being by weight and the abbreviation K-EDTA used therein meaning the potassium salt of ethylenediaminetetraacetic acid.

EXAMPLE 1

Synthesis of the 1-arylsemicarbazides

General Procedure

The synthesis starts from appropriate aromatic amines which are diazotised to give the corresponding diazonium compounds. The diazonium salt is converted into the corresponding hydrazine in hydrochloric acid solution by means of stannous chloride. Reaction of the hydrazine hydrochloride or of the free hydrazine base in glacial acetic acid with potassium cyanate gives the desired 1-arylsemicarbazide in good yield.

In the following Tables, there are set out some of the 1-arylsemicarbazides which can be used according to the present invention, some of which are new. Those which are new are indicated with an asterisk.

TABLE I $$Ar-NH-NH-\overset{O}{\underset{\|}{C}}-NH_2$$

| Ar | m.p. | Literature reference |
|---|---|---|
| 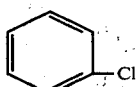 | 168°–170° | * |
| 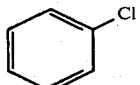 | 151°–153° | J. T. Hewitt, J. Chem. Soc., 868/1873 |
| 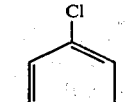 | 228°–231° | J. T. Hewitt, J. Chem. Soc., 209/1891 |

TABLE I-continued $$\text{Ar}-\text{NH}-\text{NH}-\overset{\overset{\text{O}}{\|}}{\text{C}}-\text{NH}_2$$

| Ar | m.p. | Literature reference |
|---|---|---|
| 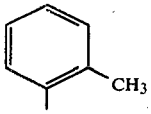 | 159° | J. V. Janowski, J. Reimann, Ber. 21, 1221/1888 |
| 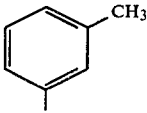 | 182° | * |
| 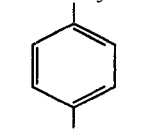 | 188° | * |
| 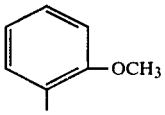 | 216° | * |
| 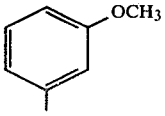 | 135° | * |
| 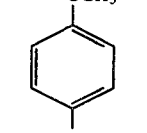 | 179° | * |
| 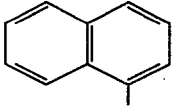 | 231° | A. Pinner, Ber. 21, 1222/1888 |
| 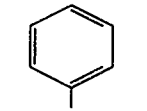 | 170°–173° | Commercial product of E. Merck |

EXAMPLE 2

Test for the detection of occult blood in feces

Filter paper (Schleicher & Schull 597 NF-Ind.) is successively impregnated with the following solutions and dried:

Solution 1

| 0.34 molar K-EDTA buffer, pH 5.5 | 10 ml. |
|---|---|
| polyvinylpyrrolidone | 300 mg. |
| distilled water | ad 100 ml. |

Solution 2

| guaiaconic acid A, $E_{1\ cm.}^{1\%} = 260$ at 600 nm | 130 mg. |
|---|---|
| 1-phenylsemicarbazide | 65 mg. |
| acetone | ad 100 ml. |

Instead of 1-phenylsemicarbazide, there can be used an equimolar amount of any of the other compounds mentioned in Example 1.

The concentrations of the 1-arylsemicarbazides can vary within the range of ±30% by weight, referred to the above-given amounts, without the sensitivity of the detection reaction being markedly influenced or without the stabilizing effect being changed.

Test papers which have been produced by the process described in this Example are stable towards the influences of light and air and are outstandingly useful for the detection of pathological amounts of blood in feces. For this purpose, feces are applied to the test paper, allowed to dry and developed from the rear side with an alcoholic solution of hydrogen peroxide. If pathological amounts of blood are present, then a bright blue colored zone results which radiates out from the sample.

EXAMPLE 3

Experiments for the Stabilization of Quaiaconic Acid A by Known Anti-oxidants (Test for Blood in Feces)

Filter paper (Schleicher & Schull 597 NF-Ind.) is successively impregnated with the following solutions and then dried:

Solution 1

| 0.34 molar K-EDTA buffer, pH 5.5 | 10 ml. |
|---|---|
| polyvinylpyrrolidone | 300 mg. |
| distilled water | ad 100 ml. |

Solution 2

| guaiaconic acid A, $E_{1\ cm.}^{1\%} = 260$ at 600 nm | 130 mg. |
|---|---|
| antioxidant | 60 mg. |
| ethanol | ad 100 ml. |

As antioxidants, there are used 2,6-di-tert.-butyl-p-cresol, gallic acid, gallic acid esters, pyrocatechol, 2,6-di-tert.-butyl-phenol, 2,6-dihydroxybenzoic acid, gentisic acid, nordihydroguaiaretic acid, N-phenyl-α-naphthylamine, triphenyl phosphine, benzimidazole and 2,2-bis-(4-hydroxyphenyl)-propane.

The papers so produced are compared with papers which have been produced according to Example 2 and tested for their usefulness for the detection of pathological amounts of blood in feces. All antioxidants act in such a manner that they suppress the detection of pathological amounts of blood in feces.

If the concentration of the antioxidant in the formulation is reduced to such an extent that there is again obtained a sufficient sensitivity of the test, then these substances lose their stabilizing action.

EXAMPLE 4

Detection of Blood in Feces

Filter paper (Whatman No.1) is successively impregnated with the following solutions and then dried:

Solution 1

| 0.34 molar K-EDTA buffer, pH 5.0 | 10 ml. |
|---|---|
| dioctyl sodium sulphosuccinate | 500 mg. |
| methanol | 20 ml. |

| | |
|---|---|
| distilled water | 80 ml. |

Solution 2

| | |
|---|---|
| 3,3',5,5'-tetramethylbenzidine | 400 mg. |
| 1-phenylsemicarbazide | 100 mg. |
| acetone | 100 ml. |

A test paper produced in this manner fully satisfies the requirements which are demanded of a test for the detection of pathological amounts of blood in feces.

After the development of a sample of feces applied to the test paper by means of an alcoholic solution of hydrogen peroxide, pathological amounts of blood are detected. A green color forming round the sample indicates the blood. The test paper is sufficiently stable towards light and atmospheric oxidation.

A test paper which has been produced according to the above formulation but without the use of the 1-arylsemicarbazide according to the present invention, on the other hand, becomes blue-green colored within a short period of time in light and air. It can no longer be used for diagnostic purposes.

EXAMPLE 5

Detection of Blood in Feces

Filter paper (Schleicher & Schull 597 NF-Ind.) is successively impregnated with the following solutions and then dried:
Solution 1
Corresponds to Solution 1 of Example 4.
Solution 2

| | |
|---|---|
| 1-[(3-ethylbenzthiazolone-(2)]-2-[1-phenyl-3-methyl-4-ethyl-1,2,4-triazolone-(5)]-azine | 100 mg. |
| 1-phenylsemicarbazide | 70 mg. |
| acetone | 100 ml. |

Such a paper has the same properties as one produced according to Example 3; the resulting reaction color is blue. Papers which have been produced without the addition of the 1-arylsemicarbazide according to the present invention become discolored even during the detection reaction in such a manner that, even in the case of feces of healthy subjects, a falsely positive reaction can be simulated.

EXAMPLE 6

Test Paper for the Detection of Blood in Urine or Liquor

Filter paper (Schleicher & Schull 23 SL) is successively impregnated with the following solutions and then dried:
Solution 1

| | |
|---|---|
| 1.2 molar sodium citrate buffer, pH 5.25 | 35 ml. |
| ethylenediamine-tetraacetic acid disodium salt | 0.1 g. |
| dioctyl sodium sulphosuccinate | 0.5 g. |
| 2,5-dimethylhexane-2,5-dihydroperoxide (about 70%) | 1.6 g |
| phosphoric acid trimorpholide | 12.7 g. |
| ethanol | 30.0 ml. |

| | |
|---|---|
| distilled water | ad 100 ml. |

Solution 2

| | |
|---|---|
| 3,3',5,5'-tetramethylbenzidine | 0.3 g. |
| phenanthridine | 0.2 g. |
| 1-phenylsemicarbazide | 0.05 g. |
| methanol/toluene (40:60 v/v) | ad 100 ml. |

Test papers of this kind are practically not influenced by light and air. Test papers without the 1-arylsemicarbazide used according to the present invention become green colored after illumination for 5 to 10 minutes. Papers in which, instead of the 1-arylsemicarbazide used according to the present invention, an equimolar amount of aminoguanidine or of semicarbazide has been introduced into the impregnation solution have equally unfavorable properties.

The 1-phenylsemicarbazide can be replaced by equimolar amounts of 1-(p-chlorophenyl)-semicarbazide, 1-(p-tolyl)-semicarbazide or 1-(p-methoxy)-semicarbazide, without altering the properties of the papers. Blood can be detected with sufficient sensitivity in urine or in liquor with the papers produced according to this Example.

EXAMPLE 7

Test Papers for the Detection of Glucose in Urine.

Filter paper (Schleicher & Schull 2312) is successively impregnated with the following solutions and then dried:
Solution 1

| | |
|---|---|
| glucose oxidase (55 U/mg.) | 500 mg. |
| peroxidase (75 U/mg.) | 200 mg. |
| tartrazine | 100 mg. |
| distilled water | 100 ml. |

Solution 2

| | |
|---|---|
| 3,3',5,5'-tetramethylbenzidine | 600 mg. |
| 1-phenylsemicarbazide | 50 mg. |
| sodium lauryl sarcosinate | 100 mg. |
| distilled water | 100 ml. |

A paper produced in this manner is stable towards the influences of light, air and atmospheric moisture and, with glucose concentrations of 30 mg. to 2000 mg. per dl. of urine, shows an increasingly intensive green indicator reaction. If, in the production of the paper, the 1-arylsemicarbazide used according to the present invention is omitted, then papers are obtained which are sensitive to light, air and atmospheric humidity. Within a short period of time, they become discolored so that, in the case of the detention of glucose in urine, falsely positive reactions can occur.

EXAMPLE 8

Test Paper for the Detection of Glucose in Urine

Filter paper (Schleicher & Schull 2316) is impregnated with a solution of the following composition and then dried:

| | |
|---|---|
| disodium salt of 2,2'-azino-di-[1-ethyl-quinoline-(2)-di-sulphonic acid-(6)] | 100 mg. |
| 1-phenylsemicarbazide | 50 mg. |
| polyvinylpyrrolidone | 250 mg. |
| glucose oxidase (50 U/mg.) | 400 mg. |
| peroxidase (75 U/mg.) | 100 mg. |
| 0.4 molar sodium citrate buffer, pH 5.0 | 100 ml. |

A paper produced in this manner permits the detection of glucose concentrations in urine above about 50 mg./dl. by means of a coloration towards violet. It is not discolored in light and air. However, papers which have been produced without the addition of the 1-arylsemicarbazide used according to the present invention became discolored due to the action of light and air.

It will be understood that the specification and examples are illustrative, but not limitative of the present invention and that other embodiments within the spirit and scope of the invention will suggest themselves to those skilled in the art.

What is claimed is:

1. In a diagnostic agent for the detection of (a) hydroperoxides or of substances which react with the liberation of hydroperoxides or of (b) peroxidase or of peroxidatively-active substances, comprising a stabilized oxidation indicator and, in case (a), peroxidase or a peroxidatively active substance or, in case (b), hydroperoxide or a substance which reacts with the liberation of hydroperoxides, the improvement which comprises, in a stabilizing amount, a 1-arylsemicarbazide of the formula Ar—NH—NH—CO—NH$_2$ in which Ar is aryl or aryl substituted with alkyl, alkoxy or halogen.

2. In a diagnostic agent as claimed in claim 1 for the detection of hydroperoxides or of substances which react with the liberation of hydroperoxides which diagnostic agent comprises a stabilized oxidation indicator and peroxidase or a peroxidatively active substance, the improvement comprising said 1-arylsemicarbazide.

3. In a diagnostic agent as claimed in claim 1 for the detection of peroxidase or a peroxidatively active substance comprising a stabilized oxidation indicator and hydroperoxide or a substance which reacts with the liberation of hydroperoxides, the improvement comprising said 1-arylsemicarbazide.

4. In a diagnostic agent as claimed in claim 1 for the determination of glucose in body fluids, wherein the oxidation indicator used is a benzidine or azine compound, the improvement comprising said 1-arylsemicarbazide.

5. In a diagnostic agent as claimed in claim 1 for the determination of occult blood in feces, wherein the oxidation indicator used is a guaiaconic acid A with the specific extinction $E_{1cm}^{1\%}$ at 600 nm of at least 200, determined by the reaction of peroxidase and hydrogen peroxide, or is a benzidine or azine compound, the improvement comprising said 1-arylsemicarbazide.

6. In a diagnostic agent as claimed in claim 1 wherein the components are impregnated on to an absorbent carrier, the improvement comprising said 1-arylsemicarbazide.

7. In a diagnostic agent as claimed in claim 1 wherein there is also present at least one additional adjuvant selected from buffers, wetting agents, thickening agents, protective colloids and complex formers, the improvement comprising said 1-arylsemicarbazide.

* * * * *